United States Patent [19]
Seino et al.

[11] Patent Number: 5,919,692
[45] Date of Patent: Jul. 6, 1999

[54] UBIQUITOUS ATP-SENSITIVE POTASSIUM-CHANNEL GENES

[75] Inventors: Susumu Seino; Nobuya Inagaki, both of Chiba, Japan

[73] Assignees: Susumu Seino, Chiba; JCR Pharmaceuticals Co., Ltd., Hyogo, both of Japan

[21] Appl. No.: 08/614,155

[22] Filed: Mar. 12, 1996

[30] Foreign Application Priority Data

Sep. 18, 1995 [JP] Japan ................................... 7-264942

[51] Int. Cl.$^6$ .............................. C12N 1/21; C12N 5/10; C12N 15/11; C12N 15/63
[52] U.S. Cl. ..................... 435/252.3; 435/320.1; 435/254.11; 435/325; 536/23.1; 536/23.4; 536/23.5; 536/24.3; 536/24.31; 536/24.32
[58] Field of Search ................... 536/23.1, 23.5, 536/23.4, 24.3, 24.31, 24.32; 435/320.1, 69.1, 172.3, 252.3, 254.11, 325, 410, 6; 800/2, 200

[56] References Cited

FOREIGN PATENT DOCUMENTS

94/19464  9/1994  WIPO .
95/04820  2/1995  WIPO .

OTHER PUBLICATIONS

Asford et al. Nature 370:456–459, Aug. 1994.
Bowie et al. Science 247:1306–1310, 1990.
Wells. Biochemistry 29:8509–8517, 1990.
Ngo et al. The Protein Folding Problem and Tertiary Structure Prediction, Merz et al., eds., Birkhauser, Boston, pp. 492–495, 1994.
J Biol Chem, Mar. 17, 1995, 270 (11) P5691–4, United States, XP002019860, Susumu Seino Inohana Shukusha Chiba University: "Cloning and functional characterization of a novel ATP—sensitive potassium channel ubiquitously expressed in rat tissues, including pancreatic islets, pituitary, skeletal muscle, and heart."
Genomics, Nov. 1, 1995, 30 (1) P102–4, United States, XP000612109 Inagaki N et al: "cDNA sequence, gene structure, and chromosomal localization of the human ATP—sensitive potassium channel, uKATP–1, gene (KCNJ8)."
"The Journal of Biochemical Chemistry", vol. 270, No. 11, issue of Mar. 17, 1995.

*Primary Examiner*—Elizabeth Kemmerer
*Attorney, Agent, or Firm*—Jacobson, Price, Holman & Stern, PLLC

[57] ABSTRACT

The present invention provides novel ATP-sensitive potassium-channel proteins which are present ubiquitously in the living bodies of animals, and their genes.

13 Claims, 5 Drawing Sheets

FIG. 1

| | | | | | |
|---|---|---|---|---|---|
| 10 MLARKSIIPE | 20 EYVLARIAAE | 30 NLRKPRIRDR | 40 LPKARFIAKS | 50 GACNLAHKNI | 60 REQGRFLQDI |
| 70 FTTLVDLKWR | 80 HTLVIFTMSF | 90 LCSWLLFAIM | 100 WWLVAFAHGD | 110 IYAYMEKSGM | 120 EKSGLESTVC |
| 130 VTNVRSFTSA | 140 FLFSIEVQVT | 150 IGFGGRMMTE | 160 ECPLAITVLI | 170 LQNIVGLIIN | 180 AVMLGCIFMK |
| 190 TAQAHRRAET | 200 LIFSRHAVIA | 210 VRNGKLCFMF | 220 RVGDLRKSMI | 230 ISASVRIQVV | 240 KKTTTPEGEV |
| 250 VPIHQLDIPV | 260 DNPIESNNIF | 270 LVAPLIICHV | 280 IDKRSPLYDI | 290 SATDLANQDL | 300 EVIVILEGVV |
| 310 ETTGITTQAR | 320 TSYIAEEIQW | 330 GHRFVSIVTE | 340 EEGVYSVDYS | 350 KFGNTVKVAA | 360 PRCSARELDE |
| 370 KPSILIQTLQ | 380 KSELSHQNSL | 390 RKRNSMRRNN | 400 SMRRNNSIRR | 410 NNSSLMVPKV | 420 QFMTPEGNQN |
| 430 TSES*......... | 440 .................. | 450 .................. | 460 .................. | 470 .................. | 480 .................. |

FIG. 3

| | | | | | |
|---|---|---|---|---|---|
| 10 MLARKSIIPE | 20 EYVLARIAAE | 30 NLRKPRIRDR | 40 LPKARFIAKS | 50 GACNLAHKNI | 60 REQGRFLQDI |
| 70 FTTLVDLKWR | 80 HTLVIFTMSF | 90 LCSWLLFAIM | 100 WWLVAFAHGD | 110 IYAYMEKGIT | 120 EKSGLESAVC |
| 130 VTNVRSFTSA | 140 FLFSIEVQVT | 150 IGFGGRMMTE | 160 ECPLAITVLI | 170 LQNIVGLIIN | 180 AVMLGCIFMK |
| 190 TAQAHRRAET | 200 LIFSRHAVIA | 210 VRNGKLCFMF | 220 RVGDLRKSMI | 230 ISASVRIQVV | 240 KKTTTPEGEV |
| 250 VPIHQQDIPV | 260 DNPIESNNIF | 270 LVAPLIICHV | 280 IDKRSPLYDI | 290 SATDLVNQDL | 300 EVIVILEGVV |
| 310 ETTGITTQAR | 320 TSYIAEEIQW | 330 GHRFVSIVTE | 340 EEGVYSVDYS | 350 KFGNTVRVAA | 360 PRCSARELDE |
| 370 KPSILIQTLQ | 380 KSELSHQNSL | 390 RKRNSMRRNN | 400 SMRRSNSIRR | 410 NNSSLMVPKV | 420 QFMTPEGNQC |
| 430 PSES*......... | 440 .................. | 450 .................. | 460 .................. | 470 .................. | 480 .................. |

FIG. 2

```
        10         20         30         40         50         60
 ATGTTGGCCA GAAAGAGTAT CATCCCGGAG GAGTATGTGC TGGCGCGCAT CGCCGCAGAG
        70         80         90        100        110        120
 AACCTGCGCA AGCCGCGCAT CCGAGACCGC CTCCCCAAAG CCCGCTTCAT CGCCAAGAGC
       130        140        150        160        170        180
 GGGGCCTGCA ACCTGGCGCA TAAGAACATC CGTGAGCAAG GACGCTTTCT ACAGGACATC
       190        200        210        220        230        240
 TTCACCACCT TGGTGGACCT GAAATGGCGC CACACGCTGG TCATCTTTAC CATGTCCTTC
       250        260        270        280        290        300
 CTCTGCAGCT GGCTGCTCTT CGCTATCATG TGGTGGCTGG TGGCCTTTGC CCATGGGGAC
       310        320        330        340        350        360
 ATCTATGCTT ACATGGAGAA AAGTGGAATG GAGAAAGTG GTTTGGAGTC CACTGTGTGT
       370        380        390        400        410        420
 GTGACTAATG TCAGGTCTTT CACTTCTGCT TTTCTCTTCT CCATTGAAGT TCAAGTTACC
       430        440        450        460        470        480
 ATTGGGTTTG GAGGGAGGAT GATGACAGAG GAATGCCCTT TGGCCATCAC GGTTTTGATT
       490        500        510        520        530        540
 CTCCAGAATA TTGTGGGTTT GATCATCAAT GCAGTCATGT TAGGCTGCAT TTTCATGAAA
       550        560        570        580        590        600
 ACAGCTCAGG CTCACAGAAG GGCAGAAACT TTGATTTTCA GCCGCCATGC TGTGATTGCC
       610        620        630        640        650        660
 GTCCGAAATG GCAAGCTGTG CTTCATGTTC CGAGTGGGTG ACCTGAGGAA AAGCATGATC
       670        680        690        700        710        720
 ATTAGTGCCT CTGTGCGCAT CCAGGTGGTC AAGAAAACAA CTACACCTGA AGGGGAGGTG
       730        740        750        760        770        780
 GTTCCTATTC ACCAACTGGA CATTCCTGTT GATAACCCAA TCGAGAGCAA TAACATTTTT
       790        800        810        820        830        840
 CTGGTGGCCC CTTTGATCAT CTGCCACGTG ATTGACAAGC GCAGTCCCCT GTATGACATC
       850        860        870        880        890        900
 TCAGCAACTG ACCTGGCCAA CCAAGACTTG GAGGTCATAG TTATTCTGGA AGGAGTGGTT
       910        920        930        940        950        960
 GAAACTACTG GCATCACCAC ACAAGCACGA ACCTCCTACA TTGCTGAGGA GATCCAATGG
       970        980        990       1000       1010       1020
 GGCCACCGCT TTGTGTCCAT TGTGACTGAG GAAGAAGGAG TGTATTCTGT GGATTACTCC
      1030       1040       1050       1060       1070       1080
 AAATTTGGCA ACACTGTTAA AGTAGCTGCT CCACGGTGCA GTGCCCGAGA GCTGGATGAG
      1090       1100       1110       1120       1130       1140
 AAACCTTCCA TCCTTATTCA GACCCTCCAA AAGAGTGAAC TGTCTCATCA AAATTCTCTG
      1150       1160       1170       1180       1190       1200
 AGGAAGCGCA ACTCCATGAG AAGAAACAAT TCCATGAGGA GGAACAATTC TATCCGAAGG
      1210       1220       1230       1240       1250       1260
 AACAATTCTT CCCTCATGGT ACCAAAGGTG CAATTTATGA CTCCAGAAGG AAATCAAAAC
      1270       1280       1290       1300       1310       1320
 ACATCGGAAT CATGA........ .......... .......... .......... ..........
```

FIG. 4

```
            10         20         30         40         50         60
     ATGCTGGCCA GGAAGAGCAT CATCCCGGAG GAGTATGTGC TGGCCCGCAT CGCGGCGGAG
            70         80         90        100        110        120
     AACCTGCGCA AACCGCGCAT CCGCGACCGC CTCCCCAAAG CCCGCTTCAT CGCCAAGAGC
           130        140        150        160        170        180
     GGAGCCTGCA ACCTGGCTCA CAAGAACATC CGAGAGCAAG GTCGCTTCCT GCAGGACATC
           190        200        210        220        230        240
     TTCACCACCT TGGTAGACCT GAAGTGGCGT CACACGCTGG TCATCTTCAC CATGTCCTTC
           250        260        270        280        290        300
     CTCTGCAGCT GGCTGCTCTT CGCTATCATG TGGTGGCTGG TGGCCTTCGC CCACGGGGAC
           310        320        330        340        350        360
     ATCTATGCTT ACATGGAGAA AGGCATCACG GAGAAGAGTG GCCTGGAGTC TGCCGTCTGT
           370        380        390        400        410        420
     GTGACCAATG TCAGGTCATT CACTTCTGCG TTTCTCTTCT CCATCGAGGT TCAAGTGACC
           430        440        450        460        470        480
     ATTGGGTTTG GAGGGAGAAT GATGACTGAG GAGTGCCCTC TGGCCATCAC GGTTTTGATT
           490        500        510        520        530        540
     CTGCAGAACA TTGTGGGTCT GATCATCAAC GCGGTCATGT TGGGCTGCAT CTTCATGAAG
           550        560        570        580        590        600
     ACGGCCCAGG CCCACAGAAG GGCAGAGACG CTGATTTTCA GCCGCCATGC TGTAATTGCG
           610        620        630        640        650        660
     GTCCGTAATG GCAAGCTGTG CTTCATGTTC CGGGTGGGTG ACCTGAGGAA AAGCATGATC
           670        680        690        700        710        720
     ATTAGCGCCT CGGTGCGCAT CCAGGTGGTC AAGAAAACCA CGACGCCAGA AGGAGAGGTG
           730        740        750        760        770        780
     GTGCCTATTC ACCAGCAGGA CATCCCTGTG GATAATCCCA TCGAGAGCAA TAACATCTTC
           790        800        810        820        830        840
     CTAGTGGCCC CTTTGATCAT CTGCCATGTG ATTGATAAGC GTAGCCCCCT GTACGATATC
           850        860        870        880        890        900
     TCAGCCACTG ACCTTGTCAA CCAAGACCTG GAGGTCATAG TGATTCTCGA GGGCGTGGTG
           910        920        930        940        950        960
     GAAACCACGG GCATCACCAC GCAAGCGCGG ACCTCCTACA TTGCAGAGGA GATCCAGTGG
           970        980        990       1000       1010       1020
     GGACACCGCT TCGTGTCGAT TGTGACTGAG GAGGAGGGAG TGTACTCTGT GGACTATTCT
          1030       1040       1050       1060       1070       1080
     AAATTTGGTA ATACTGTGAG AGTGGCGGCG CCAAGATGCA GTGCCCGGGA GCTGGACGAG
          1090       1100       1110       1120       1130       1140
     AAACCTTCCA TCTTGATTCA GACCCTCCAA AAGAGTGAAC TGTCGCACCA GAATTCTCTG
          1150       1160       1170       1180       1190       1200
     AGGAAGCGCA ACTCTATGAG AAGAAACAAC TCCATGAGGA GGAGCAACTC CATCCGGAGG
          1210       1220       1230       1240       1250       1260
     AATAACTCTT CCCTCATGGT GCCCAAGGTG CAATTCATGA CTCCAGAAGG AAACCAGTGC
          1270       1280       1290       1300       1310       1320
     CCATCAGAAT CATGA.........  .................  .................  .................
```

UBIQUITOUS ATP-SENSITIVE POTASSIUM-CHANNEL GENES

The present invention relates to proteins for novel ATP-sensitive potassium channels, hUK$_{ATP}$-1 and ruK$_{ATP}$-1, that are expressed in various tissues of human and rat origins, and to genes encoding the same. The said proteins and genes can be used as diagnostic and therapeutic agents for potassium-channel related diseases such as diabetes, hypertension and endocrine insufficiencies.

BACKGROUND OF THE INVENTION

The etiology for diabetes is known to be mostly owing to disturbances of insulin secretion in the pancreatic β-cells. Consequently, elucidation of the molecular mechanism of insulin secretion is expected to play an important role in the clarification of causes for diabetes and the development of therapeutic agents against diabetes, but no detail has yet been made known on such molecular mechanism.

It has already been made clear that the ATP-sensitive potassium channel (K$_{ATP}$) being present on the cellular membrane plays a leading role in the cellular functions such as secretions and muscular contraction by coupling the state of metabolism in the cells with the membrane potential.

The K$_{ATP}$ channel was first discovered in the cardiac muscle in 1983 [Noma, A., Nature 305:147 (1983)] and was thereafter confirmed to be present in tissues such as the pancreatic β-cell [Cook, D. L. et al., Nature 311:271 (1984), Misler, S. et al., Proc. Natl. Acad. Sci. U.S.A. 83:7119 (1986)], pituitary [Bernardi, H. et al., Proc. Natl. Acad. Sci. U.S.A., 90:1340 (1993)]. skeletal muscle [Spruce, A. E., et al., Nature, 316:736 (1985)] and brain.

In addition, it has been suggested that there exists the molecular heterogeneity of such K$_{ATP}$ channels [Ashcroft, F. M., Annu. Rev. Neurosci. 11:97 (1988)].

Particularly in the pancreatic β-cells, ATP produced by the metabolism of glucose brings about calcium ion inflow from the calcium channel by closing the K$_{ATP}$ channel to cause depolarization, resulting in secretion of insulin. As is evident from this, the K$_{ATP}$ channel plays a leading role in regulating the secretion of insulin.

The K$_{ATP}$ channel belongs to a potassium channel family exhibiting electrophysiologically inward rectification, whereby the potassium channel family exhibiting inward rectification is classified into the four subfamilies, ROMK1, IRK1, GIRK1 and cK$_{ATP}$-1, on the basis of the degree of amino acid sequence identity.

Nevertheless, there has not been clarified the molecular architecture for the K$_{ATP}$ channel in the pancreatic β-cells. In addition, no information has been disclosed on the novel ATP-sensitive potassium channels (huK$_{ATP}$-1 and ruK$_{ATP}$-1) of the present invention for the detailed protein structure and the formation of complexes with other proteins, for example, the sulfonylurea binding protein.

SUMMARY OF THE INVENTION

In order to achieve the isolation, identification and functional analyses of a novel membrane channel, there are required the sophisticated techniques, such as molecular biological technique, cellular biological technique and electro-physiological technique.

Such being the case, the present inventors made ample and full use of such techniques to isolate human and rat genomes and cDNAs encoding the novel K$_{ATP}$ channel (uK$_{ATP}$-1) expressed in different tissues of mammalians and to identify their amino acid sequences (see FIGS. 1, 2, 3 and 4). The identified uK$_{ATP}$-1 channel was expressed in the Xenopus oocyte system and mammalian cell lines.

Electrophysiological analysis demonstrated that uK$_{ATP}$-1 is an ATP-sensitive potassium channel exhibiting inward rectification. The uK$_{ATP}$-1 channel being expressed ubiquitously in tissues of mammalians inclusive of man and rats is involved in the maintenance of the membrane potential through the basal energy metabolism.

As is described in the above, the present invention relates to an ATP-sensitive potassium channel (uK$_{ATP}$-1) which is ubiquitously present in mammalians, and encompasses the ATP-sensitive potassium channel proteins, identified DNA sequences encoding the same, plasmid having such sequences incorporated therein and furthermore recombinant cells (tranformants) having such plasmid transfected therein. In addition, this invention comprises the isolated uK$_{ATP}$-1 proteins and recombinant proteins, their related materials such as agonists and antagonists, and drug designs inclusive of diagnostics and drugs for gene therapy.

DETAILED DESCRIPTION huK$_{ATP}$-1 of a human origin is composed of 324 amino acid residue (See FIG. 1 (SEQ. ID NO: 1)) with a molecular weight of 47,965, while the one of a rat origin is likewise composed of 424 amino acid residue (see FIG. 4 (SEQ. ID NO: 4)) with a molecular weight of 47,960. These two potassium channels exhibit 98% amino acid sequence identity, and such a marked homology leads us to the assumption that uK$_{ATP}$-1 performs common, structurally and functionally basic actions in all mammalian cells. Among others, uK$_{ATP}$-1 participates in the membrane potential and energy metabolism, suggesting that it could find application as a drug substance acting to prevent disturbances under unusual, extreme metabolic conditions inclusive of endocrine diseases, e.g. diabetes, starvation and ischemia.

For example, the inflow and outflow of calcium ions caused by the opening and closing of uK$_{ATP}$-1 during the onset of ischemia is closely connected with ischemic disturbances. In other words, there is a possibility that the agonists and antagonists for the opening and closing of uK$_{ATP}$-1 would constitute a suppressory agent against ischemic disturbances.

From the comparative studies of huK$_{ATP}$-1 and ruK$_{ATP}$-1 with other potassium channels for the amino acid sequence, it was confirmed that uK$_{ATP}$-1 of the present invention belongs to a novel family of the inward rectifier potassium channels; the central region of the uK$_{ATP}$-1 protein showed increased homology with other inward rectifier potassium channels. A hydropathy plot indicated the presence of two hydrophobic regions, which are composed of two transmembrane regions characteristic of the inward rectifier potassium channels and one pore region [Nicholas, C. G., Trends Pharmacol. Sci., 14:320 (1993), Jan, L. Y. and Jan, Y. N., Nature, 371:119 (1994)].

With reference to ruK$_{ATP}$-1 (Inagaki, N. et al., J. B. C., 270:5691 (1995)], it was reported that in the second intracellular region, there are two potential cAMP-dependent protein kinase phosphorylation sites (Thr-234 and Ser-385) and seven potential protein kinase C dependent phosphorylation sites (Ser-224, Thr-345, Ser-354, Ser-379, Ser-385, Ser-391 and Ser-397), while there are one (Thr-63) and four potential casein kinase II dependent phosphorylation sites (Thr-234, Ser-281, Thr-329 and Ser-354) in the first and second intracellular regions, respectively, with no N-linked glycosylation site being present in the intracellular regions. The same findings were obtained with $huK_{ATP}$-1 [Inagaki, N., et al., in press (1995)].

Then, the present inventors identified the nucleotide sequences and entire amino acid sequences of $huK_{ATP}$-1 and $ruK_{ATP}$-1, thus enabling not only proteins themselves of $huK_{ATP}$-1 and $ruK_{ATP}$-1 but also their mutants to be synthesized in large quantities by expressing the DNAs encoding $huK_{ATP}$-1 and $ruK_{ATP}$-1 and their mutants in bacteria or animal cells with use of the known genetic engineering techniques. It is furthermore added that $huK_{ATP}$-1 and its fragments are useful for the hybridization diagnosis of depleted $huK_{ATP}$-1 DNA, with the mutants of $huK_{ATP}$-1 being of use in the studies on the sugar metabolism in cells, particularly insulin-dependent and independent diabetes.

The DNAs of novel $huK_{ATP}$-1 and $ruK_{ATP}$-1 according to the present invention were identified based on a cDNA library and genome library. The DNA encoding $huK_{ATP}$-1 shows a length of about 9.7 kb, being composed of three exons and is present on the chromosome at 12p11.23. The chromosomal DNA can be obtained by probing a genome DNA library with use of cDNAs for $uK_{ATP}$-1 and its fragment, as well. The isolated $uK_{ATP}$-1 DNA can easily be subjected to nucleotide depletion, insertion or replacement by the known techniques to prepare its mutants.

By employing the known techniques, it is easy to link nucleotide sequences encoding other proteins or synthetic polypeptides to $uK_{ATP}$-1 or its variants at the 5' and 3' ends to thereby prepare fusion proteins, or derivatives thereof.

For example, a fusion protein is prepared as a precursor protein and undergoes cleavage in vivo or in vitro to thereby perform functions; such fusion protein provides target-tissue and membrane orientation in addition to its proper function. In such a case, the fusion proteins contain sugar-chain binding amino acids, and can be modified to derivatives having tissue orientation or physiological activities activated by adding new sugar chains.

In order to produce $uK_{ATP}$-1, its mutants or their derivatives, the corresponding coding DNA is incorporated into a reproducible plasmid, and host cells being transformed with such plasmid are incubated. The host cells include bacteria, yeasts and animal cells.

Prokaryotes such as bacteria are suited for the cloning of deoxyribonucleotides. For example, pBR 322 plasmid derived from E. coli contains a gene resistant to ampicillin or tetracycline and can provide a practical means of identifying the transformed cells. Furthermore, the microbial plasmids contain a promoter which can be used to express their proteins themselves. In addition to prokaryotes, eukaryotes such as yeasts can work well, with a plasmid YRp7 being utilizable especially in allowing the expression in yeasts of the species Saccharomyces [Stinchomb et al., Nature, 282:39 (1979)].

Animal cells are also used as a host, and particularly the incubation of vertebra cells is employable easily and constitutes a conventional means [Krause and Paterson, Tissue Culture, Academic Press (1973)]. As the cell lines, there are mentioned AtT-20, Hela cells, Chinese hamster ovary (CHO), COMSM6, COS-7 and the like. The promoters of Polyomavirus. Adenovirus 2, Cytomegalovirus and Simian virus 40 are used to control the function of expression plasmid in such cell lines, wherein pCMV is a plasmid which finds widened application in the expression systems of animal cells [Thomsen et al., PNAS, 81:659 (1984)].

The DNA sequences for the channel protein and $huK_{ATP}$-1 and $muK_{ATP}$-1 according to the present invention begin with the initiation codon "ATG". In cases where the recombinant cells are used to synthesize such protein, there is no need to add ATG to the desired DNA, thus making the manipulation easy. When $uK_{ATP}$-1 is expressed in a prokaryote transformed with E. coli, consequently, there is generally synthesized a protein of the amino acid sequence beginning with Met. The N-terminated met of the resultant protein may be eliminated according to the purpose of application.

In cases in which $uK_{ATP}$-1 is synthesized in recombinant animal cells, similarly, proteins having Met contained or eliminated at the N-terminal are bio-synthesized, and both are useful for individually intended application purposes.

$uK_{ATP}$-1 and its fragments can be administered to animals for their immunization to thereby produce antibodies. Also, immunization of animals permits a monoclonal antibody to be produced from cells secreting the desired antibody.

It has become easy to prepare $uK_{ATP}$-1 in large quantities, thus providing better understanding of the same at the molecular level. Accordingly, the production of $uK_{ATP}$-1 and its mutants or analogs raises the possibility to develop diagnostics or therapeutics for the channel-protein related diseases.

In particular, such proteins can be utilized in the procedures of investigating into a substance suited for diagnostics and therapeutics, or a substance that exerts agonistic or antagonistic action on $uK_{ATP}$-1. For example, a testing procedure with animal cells can be conducted by injecting cDNA for $uK_{ATP}$-1 into cells to conduct expression, followed by addition of sulfonylurea to study their interactions [Kayano, T. et al., J. Biol. Chem., 265:13276 (1990), Example 4].

Additionally, the pertinent information has been obtained on the DNA sequence of $uK_{ATP}$-1, facilitating DNA or RNA encoding their fractional sequences to be prepared. Such relatively short DNA sequences possess the capability to hybridize with the gene to be selected, and can find application as a probe, which probe is effective for detection of cDNAs in different tissues.

The probe as prepared with use of $uK_{ATP}$-1 can be utilized to produce nucleic acids capable of hybridization from a variety of organisms and their tissues. The resultant nucleic acids may be the same type as $uK_{ATP}$-1 or its isoform and include nucleic acids encoding the novel proteins.

The prepared probe is utilizable in the gene diagnosis of potassium-channel related diseases; investigation can be conducted into patients' nucleotide sequences hybridized with the probe capable of detecting the disease genes.

The blocker and opener agents for the potassium channel have heretofore been used as therapeutics against diabetes and hypertension. $uK_{ATP}$-1 and its mutants, their derivatives and monoclonal antibodies to them, when processed into pharmaceutical preparations, can be administered to patients to thereby alleviate through neutralization the adverse effects brought about by an excess of such blocker or opener agents administered clinically. When $uK_{ATP}$-1 itself shows functional insufficiency, such pharmaceutical preparations can be administered to thereby make up for such deficient functions of $uK_{ATP}$-1.

The present invention comprises the preparation of drugs for gene therapy being applicable in the essential treatment method. The nucleotide sequences for $uK_{ATP}$-1 or its mutants and their derivatives can be incorporated into plasmid or stem cells, which are then given patients to open up the possibility of finding application as a drug for gene therapy.

Below described are the examples to illustrate the present invention in more detail, while referring to the appended drawings.

BRIEF DESCRIPTION OF THE DRAWINGS

FIG. 1 (SEQ. ID NO: 1) is an illustration of the amino acid sequences corresponding to the base sequences as shown in FIG. 2 (SEQ. ID NO: 2).

FIG. 2 (SEQ. ID NO: 2) is an illustration of the base sequence of $uK_{ATP}$-1 of a human origin as obtained in Example 5.

FIG. 3 (SEQ. ID NO: 3) is an illustration of the amino acid sequence corresponding to FIG. 4.

FIG. 4 (SEQ. ID NO: 4) is an illustration of the base sequence of $ruK_{ATP}$-1 of a FIG. 5A shows the results of electrophysiological analysis of $ruK_{ATP}$-1 with use of Xenopus oocytes. The oocytes injected with cRNA of $ruK_{ATP}$-1 exhibited inward rectification under conditions of 45 mM [$K^+$] concentrated extracellular fluid, which rectification was however blocked with 300 μM of $Ba^{2+}$ added to the extracellular fluid. The control, which comprised injection of water, was observed to produce negligible slight inward electric current alone.

EXAMPLE 1
cDNA cloning of a novel inward rectifier potassium channel ($ruK_{ATP}$-1)

A cDNA fragment of GIRK, rat G protein regulating, inward rectifier potassium channel, was amplified by the polymerase chain reaction (PCR) method. Using a $^{32}$P-labeled rat GIRK cDNA fragment as a probe, search was made into a cDNA library made from rat islets of Langerhans in the vector of λgt22. The isolated $ruK_{ATP}$-1 cDNA was cut into suitable DNA fragments, and after subcloning into M13mp18 or mp19, base sequencing was performed by the chain terminator method (see FIGS. 5 and 6).

EXAMPLE 2
Expression in Xenopus laevis oocytes and electrophysiological analysis A 20 ng quantity of cRNA synthesized in vitro from plasmid pGEM11Z containing a full-length $ruK_{ATP}$-1 cDNA with the RNA polymerase after being linearized through treatment with a restriction enzyme Not1 was injected into Xenopus oocytes, followed by electrophysiological analysis 2 or 3 days later. (see FIG. 7). As is illustrated in FIGS. 7A and 7B, there was observed a $K^+$ electric current showing weak inward rectification. The $K^+$ electric current was suppressed by adding $Ba^{2+}$ in the exracellular fluid.

EXAMPLE 3
Single-channel analysis of HEK 239 cells having $ruK_{ATP}$-1 expressed HEK 239 cells were cultured in minimum essential Eagle's medium supplemented with 10% of horse serum. The expression plasmid (pCMV6b) carrying a full-length $ruK_{ATP}$-1 coding cDNA was transfected into HEK 239 cells with use of Lipofectamine to prepare transformed HEK 293 cells. The transformed cells produced in this manner were subjected to single channel analysis, with the results being shown in FIGS. 6A and 6B.

Figure 5A:
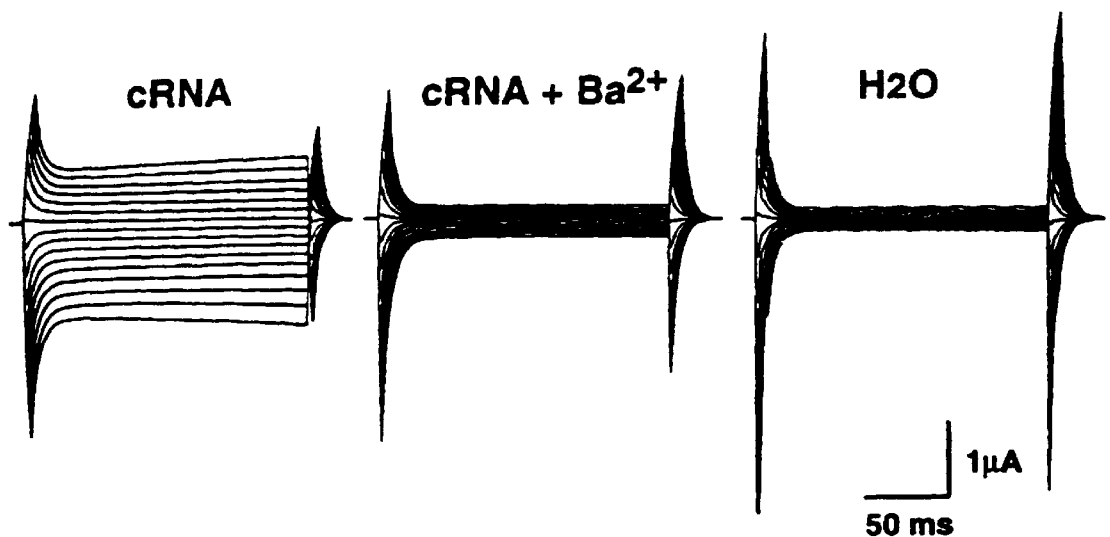
FIG. 5B is a plot of potassium-concentration dependent electric current versus voltage, leading to the confirmation that the $uK_{ATP}$-1 evidently is an inward rectifier potassium channel.
FIG. 5C is a plot of reversible voltage versus a logarithm of extracellular $K^+$ concentration in the oocyte injected with cRNA for $ruK_{ATP}$-1, indicating the dependency of the reversible voltage on the extracellular $K^+$ concentration.
Figure 5B:
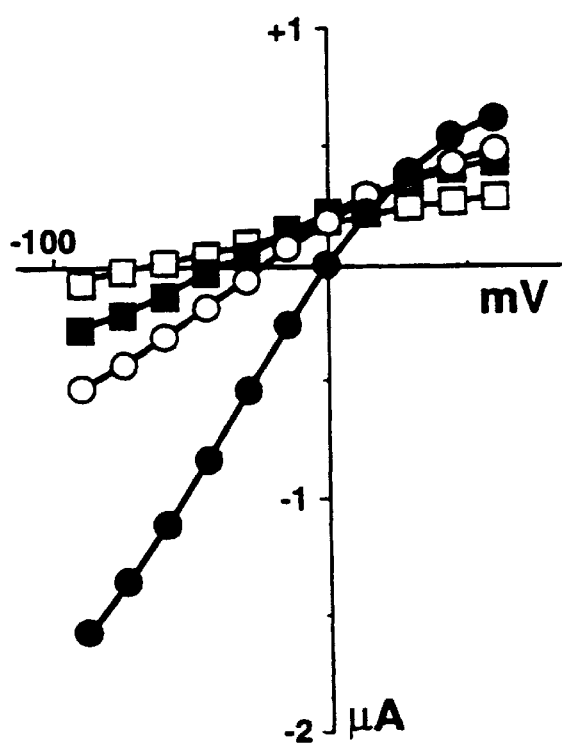
Figure 5C:
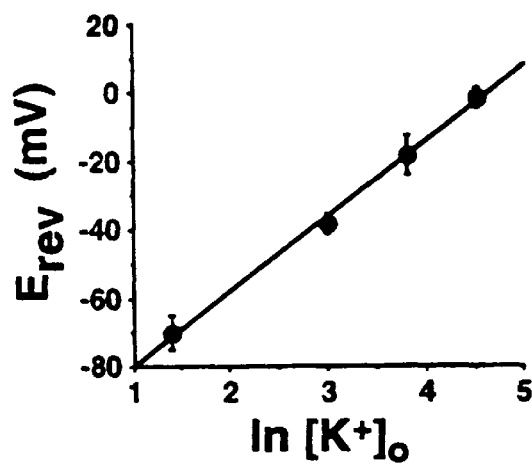
Figure 6A:
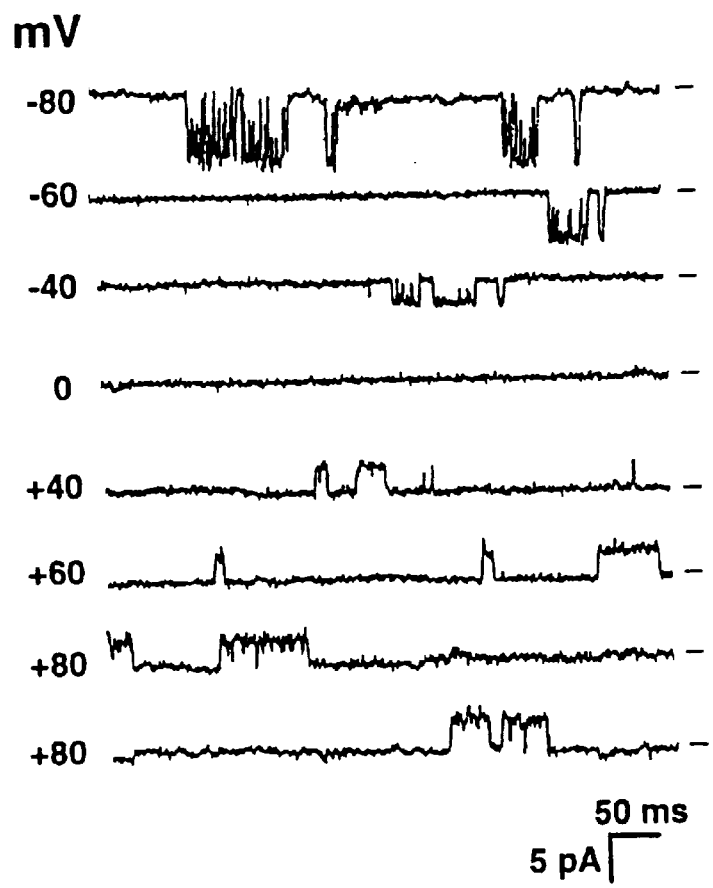
FIG. 6 is a single-channel analysis of HEK 239 transformed cells having $uK_{ATP}$-1 expressed therein, wherein A represents recordings of single-channel current and B is a current-voltage relationship, demonstrating the presence of a $K^+$ current showing inward rectification.
Figure 6B:
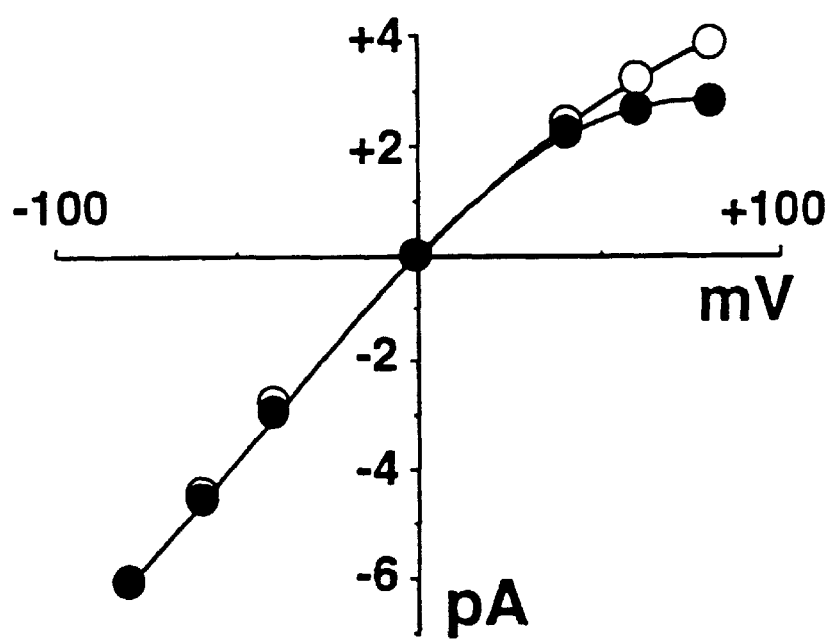

As is evident in FIGS. 8A and 8B, the outward electric current flowing through the channel was suppressed by the intracellular $Mg^{2+}$, revealing that $uK_{ATP}$-1 is an inward rectifier $K^+$ channel; $uK_{ATP}$-1 exhibited a single-channel conductance of ca. 70 pS. FIG. 5 illustrates effects of ATP on the $uK_{ATP}$-1 channel activity as observed in the inside-out mode. When 1 μM of ATP was added inside the cellular membrane, the channel was open but closed completely upon addition 1 mA of ATP. The results indicate that $uK_{ATP}$-1 is an ATP-regulated $K_{ATP}$ channel.

EXAMPLE 4
RNA Blotting analysis

A 20 μg portion of RNA extracted individually from various tissues and cell lines as well as 10 μg of RNA extracted from the pituitary and thyroid glands were denatured with formaldehyde and electrophoresed on 1% agarose gel, followed by transferring onto a Nylon membrane. Using $^{32}$P labeled $ruK_{ATP}$-1 cDNA as a probe, hybridization was carried out, with the expression of $uK_{ATP}$-1 mRNA being observed in almost all tissues.

EXAMPLE 5
Cloning of cDNA and gene of $uK_{ATP}$-1 of a human origin

In order to isolate cDNA encoding $uK_{ATP}$-1 of a human origin, search was effected into a human lung cDNA library using $^{32}$P labeled $ruK_{ATP}$-1 cDNA of a rat origin as a probe. The resultant clone was subjected to sub-cloning into M13mp18, M13mp19 and pGEM3Z, followed by base sequencing by the chain terminator method.

---

We claim:

1. A isolated deoxyribonucleic acid molecule comprising a base sequence encoding a protein having amino acid SEQ. ID NO:1.

2. The deoxyribonucleic acid molecule of claim 1 having a base sequence represented by SEQ. ID NO:2.

3. The deoxyribonucleic acid molecule of claim 1 wherein the protein exhibits the biological activity of an ATP-sensitive potassium channel protein, said molecule further comprising a base sequence encoding another protein or polypeptide linked to either the 5' end or 3' end of said molecule.

4. The deoxyribonucleic acid molecule of claim 3 having the base sequence represented by SEQ. ID NO:4.

5. An expression plasmid comprising the deoxyribonucleic acid of claim 3 operatively linked to a promoter.

6. An isolated cell transfected with the plasmid of claim 5.

7. An expression plasmid comprising the deoxyribonucleic acid of claim 1 disposed downstream of the promoter of said plasmid.

8. An isolated cell transfected with the plasmid of claim 7.

9. A isolated deoxyribonucleic acid molecule comprising a base sequence encoding the amino acid sequence of SEQ. ID NO:3.

10. An expression plasmid comprising the deoxyribonucleic acid of claim 9 operatively linked to a promoter.

11. An isolated cell transfected with the plasmid of claim 10.

12. An isolated DNA probe comprising a fragment of a nucleic acid sequence encoding the amino acid sequence of SEQ ID NO:1, said fragment having sufficient length to hybridize specifically with said nucleic acid sequence.

13. An isolated DNA probe comprising a fragment of a nucleic acid sequence encoding the amino acid sequence of SEQ ID NO:3, said fragment having sufficient length to hybridize specifically with said nucleic acid sequence.

* * * * *

UNITED STATES PATENT AND TRADEMARK OFFICE
CERTIFICATE OF CORRECTION

PATENT NO. : 5,919,692
DATED : July 6, 1999
INVENTOR(S) : Seino et al.

It is certified that error appears in the above-identified patent and that said Letters Patent is hereby corrected as shown below:

Column 2, line 23, change "324" to --424--

Column 3, line 60, change "COMSM6" to --COSM6--

Column 3, line 67, change "muK$_{ATP}$" to --ruK$_{ATP}$--

Column 4, line 27, change "cDNA" to --cRNA--

Signed and Sealed this

Ninth Day of January, 2001

*Attest:*

*Attesting Officer*

Q. TODD DICKINSON

*Commissioner of Patents and Trademarks*

SEQUENCE LISTING (1) GENERAL INFORMATION:

(iii) NUMBER OF SEQUENCES:    4

(2) INFORMATION FOR SEQ ID NO: 1:

(i) SEQUENCE CHARACTERISTICS:
      (A) LENGTH:   424 amino acids
      (B) TYPE:   amino acid
      (C) STRANDEDNESS:   single
      (D) TOPOLOGY:    linear (xi) SEQUENCE DESCRIPTION: SEQ ID NO: 1:

Met Leu Ala Arg Lys Ser Ile Ile Pro Glu Glu Tyr Val Leu Ala Arg
                  5                  10                  15

Ile Ala Ala Glu Asn Leu Arg Lys Pro Arg Ile Arg Asp Arg Leu Pro
                 20                  25                  30

Lys Ala Arg Phe Ile Ala Lys Ser Gly Ala Cys Asn Leu Ala His Lys
             35                  40                  45

Asn Ile Arg Glu Gln Gly Arg Phe Leu Gln Asp Ile Phe Thr Thr Leu
         50                  55                  60

Val Asp Leu Lys Trp Arg His Thr Leu Val Ile Phe Thr Met Ser Phe
65                  70                  75                  80

Leu Cys Ser Trp Leu Leu Phe Ala Ile Met Trp Trp Leu Val Ala Phe
                 85                  90                  95

Ala His Gly Asp Ile Tyr Ala Tyr Met Glu Lys Ser Gly Met Glu Lys
                100                 105                 110

Ser Gly Leu Glu Ser Thr Val Cys Val Thr Asn Val Arg Ser Phe Thr
             115                 120                 125

Ser Ala Phe Leu Phe Ser Ile Gln Val Gln Val Thr Ile Gly Phe Gly
         130                 135                 140

Gly Arg Met Met Thr Glu Glu Cys Pro Leu Ala Ile Thr Val Leu Ile
145                 150                 155                 160

Leu Gln Asn Ile Val Gly Leu Ile Ile Asn Ala Val Met Leu Gly Cys
                165                 170                 175

Ile Phe Met Lys Thr Ala Gln Ala His Arg Arg Ala Glu Thr Leu Ile
                180                 185                 190

Phe Ser Arg His Ala Val Ile Ala Val Arg Asn Gly Lys Leu Cys Phe
             195                 200                 205

Met Phe Arg Val Gly Asp Leu Arg Lys Ser Met Ile Ile Ser Ala Ser
         210                 215                 220

Val Arg Ile Gln Val Val Lys Lys Thr Thr Thr Pro Glu Gly Glu Val
225                 230                 235                 240

Val Pro Ile His Gln Leu Asp Ile Pro Val Asp Asn Pro Ile Glu Ser
                245                 250                 255

Asn Asn Ile Phe Leu Val Ala Pro Leu Ile Ile Cys His Val Ile Asp
                260                 265                 270

Lys Arg Ser Pro Leu Tyr Asp Ile Ser Ala Thr Asp Leu Ala Asn Gln
             275                 280                 285

Asp Leu Glu Val Ile Val Ile Leu Glu Gly Val Val Glu Thr Thr Gly
         290                 295                 300

Ile Thr Thr Gln Ala Arg Thr Ser Tyr Ile Ala Glu Glu Ile Gln Trp
305                 310                 315                 320

Gly His Arg Phe Val Ser Ile Val Thr Glu Glu Gly Val Tyr Ser
                325                 330                 335

Val Asp Tyr Ser Lys Phe Gly Asn Thr Val Lys Val Ala Ala Pro Arg
             340                 345                 350

Cys Ser Ala Arg Glu Leu Asp Glu Lys Pro Ser Ile Leu Ile Gln Thr
         355                 360                 365

Leu Gln Lys Ser Glu Leu Ser His Gln Asn Ser Leu Arg Lys Arg Asn
370                 375                 380

Ser Met Arg Arg Asn Asn Ser Met Arg Arg Asn Asn Ser Ile Arg Arg
385                 390                 395                 400

Asn Asn Ser Ser Leu Met Val Pro Lys Val Gln Phe Met Thr Pro Glu
                405                 410                 415

Gly Asn Gln Asn Thr Ser Glu Ser
            420

(2) INFORMATION FOR SEQ ID NO: 2:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (xi) SEQUENCE DESCRIPTION: SEQ ID NO: 2:

| | | |
|---|---|---|
| ATGTTGGCCA GAAAGAGTAT CATCCCGGAG GAGTATGTGC TGGCGCGCAT CGCCGCAGAG | 60 |
| AACCTGCGCA AGCCGCGCAT CCGAGACCGC CTCCCCAAAG CCCGCTTCAT CGCCAAGAGC | 120 |
| GGGGCCTGCA ACCTGGCGCA TAAGAACATC CGTGAGCAAG GACGCTTTCT ACAGGACATC | 180 |
| TTCACCACCT TGGTGGACCT GAAATGGCGC CACACGCTGG TCATCTTTAC CATGTCCTTC | 240 |
| CTCTGCAGCT GGCTGCTCTT CGCTATCATG TGGTGGCTGG TGGCCTTTGC CCATGGGGAC | 300 |
| ATCTATGCTT ACATGGAGAA AAGTGGAATG GAGAAAAGTG GTTTGGAGTC CACTGTGTGT | 360 |
| GTGACTAATG TCAGGTCTTT CACTTCTGCT TTTCTCTTCT CCATTGAAGT TCAAGTTACC | 420 |
| ATTGGGTTTG GAGGGAGGAT GATGACAGAG GAATGCCCTT TGGCCATCAC GGTTTTGATT | 480 |
| CTCCAGAATA TTGTGGGTTT GATCATCAAT GCAGTCATGT TAGGCTGCAT TTTCATGAAA | 540 |
| ACAGCTCAGG CTCACAGAAG GGCAGAAACT TTGATTTTCA GCCGCCATGC TGTGATTGCC | 600 |
| GTCCGAAATG GCAAGCTGTG CTTCATGTTC CGAGTGGGTG ACCTGAGGAA AGCATGATC | 660 |
| ATTAGTGCCT CTGTGCGCAT CCAGGTGGTC AAGAAAACAA CTACACCTGA AGGGGAGGTG | 720 |
| GTTCCTATTC ACCAACTGGA CATTCCTGTT GATAACCCAA TCGAGAGCAA TAACATTTTT | 780 |
| CTGGTGGCCC CTTTGATCAT CTGCCACGTG ATTGACAAGC GCAGTCCCCT GTATGACATC | 840 |
| TCAGCAACTG ACCTGGCCAA CCAAGACTTG GAGGTCATAG TTATTCTGGA AGGAGTGGTT | 900 |
| GAAACTACTG GCATCACCAC ACAAGCACGA ACCTCCTACA TTGCTGAGGA CATCCAATGG | 960 |
| GGCCACCGCT TTGTGTCCAT TGTGACTGAG GAAGAAGGAG TGTATTCTGT GGATTACTCC | 1020 |
| AAATTTGGCA ACACTGTTAA GTAGCTGCT CCACGGTGCA GTGCCCGAGA GCTGGATGAG | 1080 |
| AAACCTTCCA TCCTTATTCA GACCCTCCAA AAGAGTGAAC TGTCTCATCA AAATTCTCTG | 1140 |
| AGGAAGCGCA ACTCCATGAG AAGAAACAAT TCCATGAGGA GGAACAATTC TATCCGAAGG | 1200 |
| AACAATTCTT CCCTCATGGT ACCAAAGGTG CAATTTATGA CTCCAGAAGG AAATCAAAAC | 1260 |
| ACATCGGAAT CATGA | 1275 |

(2) INFORMATION FOR SEQ ID NO: 3:

(i) SEQUENCE CHARACTERISTICS:
        (A) LENGTH: 424 amino acids
        (B) TYPE: amino acid
        (C) STRANDEDNESS: single
        (D) TOPOLOGY: linear (xi) SEQUENCE DESCRIPTION: SEQ ID NO: 3:

Met Leu Ala Arg Lys Ser Ile Ile Pro Glu Glu Tyr Val Leu Ala Arg
              5                  10                  15

Ile Ala Ala Glu Asn Leu Arg Lys Pro Arg Ile Arg Asp Arg Leu Pro
            20                  25                  30

Lys Ala Arg Phe Ile Ala Lys Ser Gly Ala Cys Asn Leu Ala His Lys
          35                  40                  45

Asn Ile Arg Glu Gln Gly Arg Phe Leu Gln Asp Ile Phe Thr Thr Leu
  50                  55                  60

Val Asp Leu Lys Trp Arg His Thr Leu Val Ile Phe Thr Met Ser Phe
65                  70                  75                  80

Leu Cys Ser Trp Leu Leu Phe Ala Ile Met Trp Trp Leu Val Ala Phe
            85                  90                  95

Ala His Gly Asp Ile Tyr Ala Tyr Met Glu Lys Gly Ile Thr Glu Lys
            100                 105                 110

Ser Gly Leu Glu Ser Ala Val Cys Val Thr Asn Val Arg Ser Phe Thr
            115                 120                 125

Ser Ala Phe Leu Phe Ser Ile Glu Val Gln Val Thr Ile Gly Phe Gly
            130                 135                 140

Gly Arg Met Met Thr Glu Glu Cys Pro Leu Ala Ile Thr Val Leu Ile
145                 150                 155                 160

Leu Gln Asn Ile Val Gly Leu Ile Ile Asn Ala Val Met Leu Gly Cys
                165                 170                 175

Ile Phe Met Lys Thr Ala Gln Ala His Arg Arg Ala Glu Thr Leu Ile
                180                 185                 190

Phe Ser Arg His Ala Val Ile Ala Val Arg Asn Gly Lys Leu Cys Phe
            195                 200                 205

Met Phe Arg Val Gly Asp Leu Arg Lys Ser Met Ile Ile Ser Ala Ser
210                 215                 220

Val Arg Ile Gln Val Val Lys Lys Thr Thr Thr Pro Glu Gly Glu Val
225                 230                 235                 240

Val Pro Ile His Gln Gln Asp Ile Pro Val Asp Asn Pro Ile Glu Ser
            245                 250                 255

Asn Asn Ile Phe Leu Val Ala Pro Leu Ile Ile Cys His Val Ile Asp
            260                 265                 270

Lys Arg Ser Pro Leu Tyr Asp Ile Ser Ala Thr Asp Leu Val Asn Gln
            275                 280                 285

Asp Leu Glu Val Ile Val Ile Leu Glu Gly Val Val Glu Thr Thr Gly
            290                 295                 300

Ile Thr Thr Gln Ala Arg Thr Ser Tyr Ile Ala Glu Glu Ile Gln Trp
305                 310                 315                 320

Gly His Arg Phe Val Ser Ile Val Thr Glu Glu Gly Val Tyr Ser
                325                 330                 335

Val Asp Tyr Ser Lys Phe Gly Asn Thr Val Arg Val Ala Ala Pro Arg
            340                 345                 350

Cys Ser Ala Arg Glu Leu Asp Glu Lys Pro Ser Ile Leu Ile Gln Thr
            355                 360                 365

Leu Gln Lys Ser Glu Leu Ser His Gln Asn Ser Leu Arg Lys Arg Asn
370                 375                 380

Ser Met Arg Arg Asn Asn Ser Met Arg Arg Ser Asn Ser Ile Arg Arg
385                 390                 395                 400

Asn Asn Ser Ser Leu Met Val Pro Lys Val Gln Phe Met Thr Pro Glu
                405                 410                 415

Gly Asn Gln Cys Pro Ser Glu Ser
            420

(2) INFORMATION FOR SEQ ID NO: 4:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (xi) SEQUENCE DESCRIPTION: SEQ ID NO: 4:

-continued

```
ATGCTGGCCA GGAAGAGCAT CATCCCGGAG GAGTATGTGC TGGCCCGCAT CGCGGCGGAG      60

AACCTGCGCA AACCGCGCAT CCGCGACCGC CTCCCCAAAG CCCGCTTCAT CGCCAAGAGC     120

GGAGCCTGCA ACCTGGCTCA CAAGAACATC CGAGAGCAAG GTCGCTTCCT GCAGGACATC     180

TTCACCACCT TGGTAGACCT GAAGTGGCGT CACACGCTGG TCATCTTCAC CATGTCCTTC     240

CTCTGCAGCT GGCTGCTCTT CGCTATCATG TGGTGGCTGG TGGCCTTCGC CCACGGGGAC     300

ATCTATGCTT ACATGGAGAA AGGCATCACG GAGAAGAGTG GCCTGGAGTC TGCCGTCTGT     360

GTGACCAATG TCAGGTCATT CACTTCTGCG TTTCTCTTCT CCATCGAGGT TCAAGTGACC     420

ATTGGGTTTG GAGGGAGAAT GATGACTGAG GAGTGCCCTC TGGCCATCAC GGTTTTGATT     480

CTGCAGAACA TTGTGGGTCT GATCATCAAC GCGGTCATGT TGGGCTGCAT CTTCATGAAG     540

ACGGCCCAGG CCCACAGAAG GGCAGAGACG CTGATTTTCA GCCGCCATGC TGTAATTGCG     600

GTCCGTAATG GCAAGCTGTG CTTCATGTTC CGGGTGGGTG ACCTGAGGAA AAGCATGATC     660

ATTAGCGCCT CGGTGCGCAT CCAGGTGGTC AAGAAAACCA CGACGCCAGA AGGAGAGGTG     720

GTGCCTATTC ACCAGCAGGA CATCCCTGTG GATAATCCCA TCGAGAGCAA TAACATCTTC     780

CTAGTGGCCC CTTTGATCAT CTGCCATGTG ATTGATAAGC GTAGCCCCCT GTACGATATC     840

TCAGCCACTG ACCTTGTCAA CCAAGACCTG GAGGTCATAG TGATTCTCGA GGGCGTGGTG     900

GAAACCACGG GCATCACCAC GCAAGCGCGG ACCTCCTACA TTGCAGAGGA GATCCAGTGG     960

GGACACCGCT TCGTGTCGAT TGTGACTGAG GAGGAGGGAG TGTACTCTGT GGACTATTCT    1020

AAATTTGGTA ATACTGTGAG ACTGGCGGCG CCAAGATGCA GTGCCCGGGA GCTGGACGAG    1080

AAACCTTCCA TCTTGATTCA GACCCTCCAA AAGAGTGAAC TGTCGCACCA GAATTCTCTG    1140

AGGAAGCGCA ACTCTATGAG AAGAAACAAC TCCATGAGGA GGAGCAACTC CATCCGGAGG    1200

AATAACTCTT CCCTCATGGT GCCCAAGGTG CAATTCATGA CTCCAGAAGG AAACCAGTGC    1260

CCATCAGAAT CATGA                                                    1275
```